US011458042B2

(12) United States Patent
Magin et al.

(10) Patent No.: US 11,458,042 B2
(45) Date of Patent: Oct. 4, 2022

(54) BILAYERED DEVICES FOR ENHANCED HEALING

(71) Applicants: UNIVERSITY OF FLORIDA RESEARCH FOUNDATION, INC., Gainesville, FL (US); SHARKLET TECHNOLOGIES, INC., Aurora, CO (US)

(72) Inventors: Chelsea Marie Magin, Boulder, CO (US); Anthony B. Brennan, Gainesville, FL (US); Bradley Jay Willenberg, Orlando, FL (US); Gregory Scott Schultz, Gainesville, FL (US); Dylan Burton Neale, Gainesville, FL (US)

(73) Assignees: SHARKLET TECHNOLOGIES, INC., Aurora, CO (US); UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 933 days.

(21) Appl. No.: 15/568,767

(22) PCT Filed: Apr. 25, 2016

(86) PCT No.: PCT/US2016/029122
§ 371 (c)(1),
(2) Date: Oct. 23, 2017

(87) PCT Pub. No.: WO2017/011050
PCT Pub. Date: Jan. 19, 2017

(65) Prior Publication Data
US 2018/0078423 A1 Mar. 22, 2018

Related U.S. Application Data

(60) Provisional application No. 62/261,407, filed on Dec. 1, 2015, provisional application No. 62/151,936, filed
(Continued)

(51) Int. Cl.
*A61F 13/00* (2006.01)
*A61K 35/12* (2015.01)
(Continued)

(52) U.S. Cl.
CPC .. *A61F 13/00063* (2013.01); *A61F 13/00029* (2013.01); *A61F 13/022* (2013.01);
(Continued)

(58) Field of Classification Search
CPC .......... A61F 13/00063; A61F 13/00029; A61F 13/022; A61K 35/12; A61L 15/42;
(Continued)

(56) References Cited

U.S. PATENT DOCUMENTS 7,117,807 B2  10/2006  Bohn, Jr. et al.
7,143,709 B2  12/2006  Brennan et al.
(Continued)

FOREIGN PATENT DOCUMENTS

JP   H07136240 A   5/1995
JP   2003305067 A  10/2003
(Continued)

OTHER PUBLICATIONS

Butler, M. K. et al., "*Poly(butyl methacrylate-co-methacrylic acid) tissue engineering scaffold with pro-angiogenic potential in vivo.*", Journal of Biomedical Materials Research Part A Aug. 2007, vol. 82, No. 2 (Aug. 2007) pp. 265-273 (1 page).
(Continued)

*Primary Examiner* — Joseph S Del Sole
*Assistant Examiner* — John Robitaille
(74) *Attorney, Agent, or Firm* — Cantor Colburn LLP

(57) ABSTRACT

Disclosed herein is a multilayered wound dressing comprising a first layer; the first layer including channels that facilitate neovascularization of a wound; and a second layer in contact with the first layer, the second layer having the
(Continued)

same or different chemical composition as the first layer; where the second layer comprises at least one surface that has a texture and the direction of the texture is operative to facilitate cell orientation and growth. A method includes forming a first layer of a polymeric material; forming a second layer of the same polymeric material as the first layer on the first layer; and forming a textured surface of the second layer of the same polymeric material as the first layer, the textured surface being operative to facilitate directional cell growth when used in a wound dressing, where the first layer and the second layer are formed using an additive manufacturing process.

8 Claims, 7 Drawing Sheets

Related U.S. Application Data on Apr. 23, 2015, provisional application No. 62/151,875, filed on Apr. 23, 2015.

(51) Int. Cl.

| | |
|---|---|
| *A61L 27/58* | (2006.01) |
| *A61L 27/60* | (2006.01) |
| *A61L 27/50* | (2006.01) |
| *A61L 27/18* | (2006.01) |
| *A61L 15/42* | (2006.01) |
| *A61L 15/60* | (2006.01) |
| *A61F 13/02* | (2006.01) |
| *A61L 15/64* | (2006.01) |

(52) U.S. Cl.
CPC .............. *A61K 35/12* (2013.01); *A61L 15/42* (2013.01); *A61L 15/425* (2013.01); *A61L 15/60* (2013.01); *A61L 15/64* (2013.01); *A61L 27/18* (2013.01); *A61L 27/50* (2013.01); *A61L 27/58* (2013.01); *A61L 27/60* (2013.01); *A61L 2300/414* (2013.01)

(58) Field of Classification Search
CPC ........ A61L 15/425; A61L 15/60; A61L 15/64; A61L 27/18; A61L 27/50; A61L 27/58; A61L 27/60
See application file for complete search history.

(56) References Cited

U.S. PATENT DOCUMENTS

| | | | |
|---|---|---|---|
| 7,601,525 | B2 | 10/2009 | Batich et al. |
| 7,777,090 | B2 | 8/2010 | Park et al. |
| 8,337,893 | B2 | 12/2012 | Hatcher et al. |
| 8,603,982 | B2 | 12/2013 | Ooya et al. |
| 9,016,221 | B2 | 4/2015 | Brennan et al. |
| 9,045,651 | B2 | 6/2015 | Chen et al. |
| 2002/0005600 | A1* | 1/2002 | Ma ..................... G01N 30/482 264/49 |
| 2002/0111576 | A1 | 8/2002 | Greene et al. |
| 2003/0225355 | A1 | 12/2003 | Butler |
| 2005/0003146 | A1 | 1/2005 | Spath |
| 2007/0227428 | A1* | 10/2007 | Brennan ............. B81C 1/00206 114/67 R |
| 2010/0119755 | A1 | 5/2010 | Chung |
| 2010/0226943 | A1 | 9/2010 | Brennan et al. |
| 2010/0249688 | A1 | 9/2010 | Ambrosio et al. |
| 2012/0232649 | A1 | 9/2012 | Cuevas |
| 2012/0319325 | A1 | 12/2012 | Chung et al. |
| 2013/0304205 | A1 | 11/2013 | Cuevas |
| 2014/0336557 | A1* | 11/2014 | Durdag ............... A61F 13/0216 602/48 |
| 2015/0139960 | A1 | 5/2015 | Tumey et al. |
| 2015/0342725 | A1 | 12/2015 | Cuevas et al. |
| 2016/0123846 | A1 | 5/2016 | Magin et al. |
| 2017/0152338 | A1 | 6/2017 | Brennan et al. |
| 2017/0216543 | A1 | 8/2017 | Magin et al. |
| 2018/0171157 | A1 | 6/2018 | Magin et al. |
| 2018/0186061 | A1 | 7/2018 | Brennan et al. |
| 2018/0214600 | A1 | 8/2018 | Magin et al. |
| 2019/0070774 | A1 | 3/2019 | Chung et al. |
| 2019/0161627 | A1 | 5/2019 | Brennan et al. |
| 2019/0202109 | A1 | 7/2019 | Stoneberg et al. |
| 2019/0224903 | A1 | 7/2019 | Thielman et al. |
| 2019/0291308 | A1 | 9/2019 | Harvey et al. |

FOREIGN PATENT DOCUMENTS

| | | |
|---|---|---|
| WO | WO 2005/087287 A1 | 9/2005 |
| WO | WO 2007/056418 A2 | 5/2007 |
| WO | WO 2008/070625 A2 | 6/2008 |
| WO | WO 2012/122105 A1 | 9/2012 |

OTHER PUBLICATIONS

Della Roca, D. G. et al., *A Degradable, Bioactive, Gelatinized Alginate Hydrogel to Improve Stem Cell/Growth Factor Delivery and Facilitate Hearing after Nyocardial Infarction*, Medical Hypotehses 79 (2012) 573-577.

Magin, C. M., "*Chelsea M. Magin, Ph.D,*", Retrieved from the Internet: URL:http://www.ucdenver.edu/academics/colleges/Engineering/Programs/bioengineering/FacultyandStaff/Documents/Magin_CV-2016_2.pdf [retrieved on Nov. 20, 2018] p. 4; Presentation No. 7 (undated) (8 pages).

Magin, C. et al., "*Biodegradable, micropatterned wound dressings for enhanced epithelilization*", Abstracts of Papers American Chemical Society Ma. 22, 2015 Conf—249th National Meeting and Exposition of the American—Chemical—Society (ACS); Denver, CO, USA (Mar. 22-025, 2015), vol. 29, p. 35 (3 pages).

Ring, A. et al., "*Analysis of neovascularization of PEGT/PBT-copolymer dermis substitutes in balb/c-mise.*", Burns: Journal of the International Society of Burn Injuries Feb. 2006, vol. 32, No. 1 (Feb. 2006) (2 pages).

European Search Report for Application No. 16 82 4826 dated Nov. 30, 2018, 14 pages.

Wang, X. et al., "*The roles of knitting mesh-reinforced collagen-chitosan hybrid scaffold in the one-step repair of full-thickness skin defects in rates*", ACTA Biomaterialia August 201 Elsevier BV GBR, vol. 9, No. 8 (Aug. 2013) 7822-7832 (2 pages).

U.S. Appl. No. 16/346,957, filed May 2, 2019.

Magin et al.; "Biodegradable, micropatterned would dressings for enhanced epithelialization"; 249 th ACS National Meeting; Mar. 2015, 3 pages (abstract only).

Wang et al.; "The roles of knitted mesh-reinforced collagen-chitosan hybrid scaffold in the one-step repair of full-thickness skin defects in rats"; Acta Biomaterialia 9; Apr. 2013, pp. 7822-7832.

International Search Report and Written Opinion for International Application No. PCT/US2016/029122 dated Feb. 17, 2017, 16 pages.

Alberts, B. et al., *Molecular Biology of the Cell*, 3rd ed. Garland Publishing, Inc. (1994) 1188-1189.

Allan, G. G. et al., *Molecular Weight Manipulation of Chitosan I: Kinetics of Depolymerization by Nitrous Acid*, Carbohydrate Research 277 (1995) 257-272.

Bush, K. A. et al., *Development of Microfabricated Dermal Epidermal Regenerative Matrices to Evaluate the Role of Cellular Microenvironments on Epidermal Morphogenesis*, Tissue Eng Part A (2012); 18:2343-2353.

Capla, J. M. et al., *Skin Graft Vascularization Involves Precisely Regulated Regression and Replacement of Endothelial Cells Through ?Both Angiogenesis and Vasculogenesis*, Plastic and Reconstruction Surgery, 2006; 117(3): 836-44.

Domard, A. et al., *Glucosamine Oligomers: 1. Preparation and Characterization*, Int. J. Biol. Macromol. (1989) 11:297-302.

(56) References Cited

OTHER PUBLICATIONS

Erbacher, P. et al., *Chitosan-Based Vector/DNA Complexes for Gene Delivery: Biophysical Characteristics and Transfection Ability*, Pharm Res (1998) 15:1332-1339.

Giannitelli, S. M. et al., *Current Trends in the Design of Scaffold for Computer-Aided Tissue Engineering*, Acta Biomaterialia, 2014;10(2):580-94.

Harrison, R., *The Reaction of Embryonic Cells to Solid Structures*, The Journal of Experimental Zoology, 1914; 17(4): 521-544.

Hassan, R. M. et al., *Kinetics and Mechanism of sol-Gel Transformation For Polyeletrolytes of Capillary Copper Alginate Ionotropic Membranes*, Eur. Polym. J., vol. 24, No. 12, (1988) 1173-1175.

Hassan et al., *Separation of Metal Alginate Ionotropic Gels to Polymembranes With Special Evidence on the Position of Chelation in Copper Alginate Complex*, Journal of Polymer Science (1991) 29(11):1645-1648.

Li, T. et al. *Enzymatic Production of Chitosan Oligomers*, Plant Physiol. Biochem. (1995) 33:599-603.

Magin, C. M. et al., *Micropatterned Protective Membranes Inhibit Lens Epithelial Cell Migration in Posterior Capsule Opacification Model*, Translational Vision Science and Technology (2015) 4:1-8.

Marmaras, A. et al., *Topography-Mediated Apical Guidance in Epidermal Wound Healing*, Soft Matter (2012); 8:6922-6930.

Moon, J. J. et al., *Micropatterning of Poly(Ethylene Glycol Diacrylate Hydrogels With Biomolecules to Regulate and Guide Endothelial Morphogenesis*, Tissue Engineering: Part A. 2009; 15(3):579-85.

Muzarelli, R. et al. *Reconstructon of Paradontal Tissue With Chitosan*, Biomaterials (1989) 10:598-603.

Nichol, J. W. et al., *Cell-Laden Microengineered Gelatin Methacrylate Hydrogels*, Biomaterials, Jul. 2010; 31(21): 5536-5544.

Otterlei, M. et al., *Characterization of Binding and TNF-α-Inducing Ability of Chitosans on Monocytes: The Involvement of CD14*, Vaccine (1994) 12:825-832.

Pappineau, A. M. et al., *Antimicrobial Effect Of Water-Soluble Chitosans With high Hydrostatic Pressure*, Food Biotechnol. (1991) 5:45-57.

Richardson, S. C. et al., *Potential of Low Molecular Mass Chitosan as a DNA Delivery System: Biocompatibility, Body Distribution And Ability to Complex and Protect DNA*, Int J Pharm (1999) 178:231-243.

Sannan, T. et al., *Studies on Chitin,2, Effect of Deacetylation on Solubility*, Macromol. Chem. (1976), 177:3589-3600.

Singer, A. J. et al., *Cutaneous Wound Healing*, The New England Journal of Medicine, 1999; 341:738-46.

Spier, R. E. et al., *The Encyclopedia of Cell Technology*, John Wiley & Sons, Inc. (2000).

Stefonek, T. J. et al., *Immobilized Gradients of Epidermal Growth Factor Promote Accelerated and Directed Keratinocyte Migration*, Wound Repair and Regeneration, 2007; 15(6):847-55.

Uttayarat, P. et al., *Topographic Guidance of Endothelial Cells on Silicone Surfaces With Micro- to Nanogrooves: Orientation of Actin Filaments and Focal Adhesions*, J. Biomed Mater Res Part A. 2005; 75A(3):668-80.

Varum, K. M. et al., *C-N.m.r. Studies of the Acetylation Sequences in Partially N-deacetylated Chitins (Chitosans)*, Carbohydr. Res. (1991) 217 19-27.

Willenberg et al., *Gelatinized Copper-Capillary Alginate Gel Functions as an Injectable Tissue Scaffold System for Stem Cell Transplants*, Journal of Biomaterials Science 22 (2011) 1621-1637.

Guide for Care and Use of Laboratory Animals, National Institutes of Health (NIH), National Research Council, Eighth Edition (2011) 220 pages.

Sharklet; Registration Certificate; Trademark Registration No. 3616776, Registered May 5, 2009, University of Florida Research Foundation, Inc., 1 page.

\* cited by examiner

BILAYERED DEVICES FOR ENHANCED HEALING

CROSS REFERENCE TO RELATED APPLICATIONS

This application is a national phase entry of PCT/US2016/029122 filed on 25 Apr. 2016, which claims the benefit of and priority to U.S. Application No. 62/151,875 and 62/151,936, both filed Apr. 23, 2015 and U.S. Application No. 62/261,407, filed Dec. 1, 2015, the content of which are incorporated herein by reference in their entirety.

STATEMENT REGARDING FEDERALLY SPONSORED RESEARCH

This invention was made with government support under Contract/Grant Number 1R43 AR067584 awarded by the National Institutes of Health and by Contract/Grant Number N000141310443 awarded by the NAVY/Office of Naval Research. The government has rights in the invention.

BACKGROUND

This disclosure relates to bilayered devices for enhanced healing.

No clinically available dressings have all of the characteristics that are desirable for efficient full-thickness wound healing. The current standard is a skin graft that covers the affected area. However, this approach is limited by both donor site morbidity and the availability of healthy skin; thus, it is not a feasible treatment for extensive injuries. Allografts—e.g., cadaver skin or cultured epithelial cell sheets—are often used when available for temporary wound coverage. However, long culture times, fragility of grafts, and rejection rates remain substantial obstacles in allograft treatment. Although synthetic and biosynthetic grafts do not have these same drawbacks, they both lack the ability to treat the dermis and epidermis concurrently, as do all currently available full-thickness wound dressings. While synthetic skin grafts (e.g., Endoform™, Biobrane® and Integra®) are used to enhance dermal healing, these products can take up to 3 weeks to vascularize, allowing for complications to occur during that extend the timeframe for healing.

These products also do not directly promote re-epithelialization. Biobrane® and Integra®, for instance, include a silicone-based top layer that must be removed after dermal regeneration to allow epidermal healing. The need to remove this top dressing layer is a key drawback of many synthetic wound dressings. It disrupts epithelial cell migration and new tissue formation, and it increases costs and patient discomfort. In an international survey of wound-care specialists, nearly 60% said they would prefer a one-piece composite for burn treatment to reduce frequency of dressing changes.

SUMMARY

Disclosed herein is a multilayered wound dressing comprising a first layer; the first layer comprising channels that facilitate neovascularization of a wound; and a second layer in contact with the first layer, the second layer having the same or a different chemical composition as the first layer; wherein the second layer comprises at least one surface that has a texture and where the direction of the texture is operative to facilitate cell orientation and growth.

Disclosed herein too is a method comprising forming a first layer of a polymeric material; forming a second layer of the same or different polymeric material from the first layer on the first layer; and forming a textured surface on the second layer where the textured surface is operative to facilitate directional cell growth when used in a wound dressing, wherein the first layer and the second layer are formed using an additive manufacturing process. In an embodiment, an additive manufacturing process (also sometimes referred to herein as 3D printing) may be used to print a plurality of layers that are in combination a part of the first layer. As noted above, this plurality of layers may have a) different structures; b) different compositions (e.g., chemistries); or c) both different structures and chemistries and compositions. The plurality of layers may have a gradual variation in structure or composition (i.e., have a gradient in structure or composition) or alternatively, have random variations in structure or composition from one layer to another.

Disclosed herein is a method comprising disposing a multilayered wound dressing on or in a wound; where the multilayered dressing comprises a first gel layer; the first gel layer comprising channels that facilitate neovascularization when used in a wound dressing; and a second layer in contact with the first gel layer; where the second layer comprises at least one surface that has a texture; where the channels and the texture facilitate multilayered cell growth in one or more directions.

Disclosed herein too is an article comprising a first gel layer; the first gel layer comprising channels that facilitate neovascularization when used in a wound dressing; where the first layer comprises a first type of growing cell; and a second layer in contact with the first gel layer; where the second layer comprises at least one surface that has a texture; and where the second layer comprises a second type of growing cell.

Disclosed herein is a multilayered wound dressing comprising a first gel layer; the first layer comprising three-dimensional channels that facilitate neovascularization of a wound and comprising a natural or synthetic biodegradable polymer; and a second layer in contact with the first gel layer, the second layer comprising at least one surface that has a texture, the direction of the texture being operative to facilitate cell orientation and growth.

Disclosed herein too is a method comprising forming a first layer of a natural or synthetic biodegradable polymeric material; forming a second layer of a polymeric material on the first layer; and forming a textured surface of the second layer, the textured surface being operative to facilitate directional cell growth when used in a wound dressing, wherein the first layer and the second layer are formed using an additive manufacturing process.

DETAILED DESCRIPTION

Figure 1:
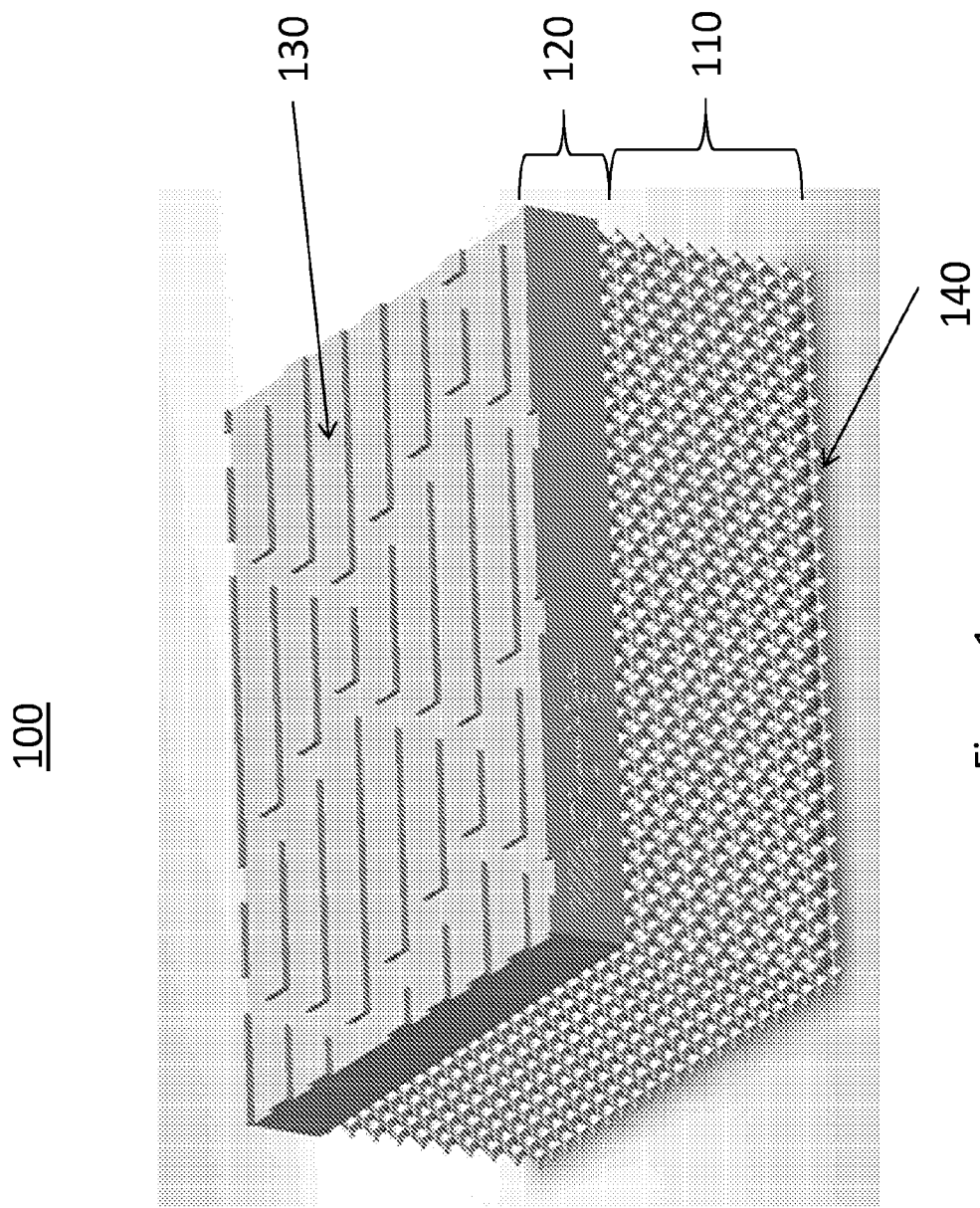
FIG. 1 shows a schematic diagram of an embodiment of the bilayered device for wound healing.

Disclosed herein is a multilayered, patterned full-thickness wound dressing that enhances neovascularization, dermal healing, and autologous epidermal healing. The dressing comprises at least two layers, a first layer of which is a vasoinductive dermal matrix layer, and a second layer of which is a patterned apical layer to guide cell migration across the wound.

In an embodiment, the first layer may comprise a plurality of layers that have different structures, compositions (e.g., chemistries), or both compositions and structures. These different structures and/or compositions may be gradual or systematic in the form of a gradient or alternatively may be random. In an embodiment, the first layer generally has a plurality of continuous three-dimensional channels that facilitate neovascularization while the texturing on the second layer facilitates directional cell growth in the wound healing dressing. The second layer is disposed on the first layer and may be in direct contact with it. The second layer has at least one surface that has a texture. The direction of the texture is operative to facilitate cell orientation and growth.

The first layer contains channels while the second layer comprises a textured surface. The orientation of the channels and the patterns in the textured surface can be varied to produce cell layers (in the first layer) having different orientations. By orienting the cells in the different layers differently, the strength of the new cell layers can be improved over the old cell layers.

By texturing a surface of the second layer, fluids that are not desired at the wound can be drained away while other desirable fluids that facilitate healing are directed to the wound. The texture in the multilayer wound dressing can also be used to mitigate or to eliminate the growth of undesirable bacteria or viruses in the proximity of the wound.

Disclosed herein too is a method of using the multilayered wound dressing in or on a wound. The use of a multilayer wound dressing permits the growth of cells in the wounded area in a single direction or in multiple directions depending upon the orientation of micropores in one of the layers and the channel orientation in another of the layers.

The term "channel" as used herein implies pathways that extend partially or completely through the first layer or the plurality of layers that constitute the first layer. These channels can include capillaries, pores, micropores, and can have cross-sectional geometries that are square, rectangular, triangular, circular, ellipsoidal, polygonal, or a combination thereof. The channels have dimensions in the nanometer range or in the micrometer range. The channels can have average cross-sectional dimensions of 10 nanometers to 10 micrometers, preferably 20 nanometers to 1 micrometer, and more preferably 50 nanometers to 5 micrometers. In some embodiments, the channels can have average cross-sectional dimensions of 10 micrometer to 1 millimeter. The larger channels allow for more fluid transport, which is useful for successful nutrient delivery to the bulk of the wound dressing. Cross-sectional dimensions are measured perpendicular to the length of the channel. The channel has an aspect ratio of greater than 2:1, preferably greater than 5:1 and more preferably greater than 10:1.

The channel may be surrounded on all sides by the material that constitutes the first layer but does not have to be surrounded on all sides by walls of the material that constitutes the first layer. Instead it can have one or more of its surfaces comprise the material that is used in the second layer. Alternatively one or more surfaces of the channel is an open surface—i.e., it is open to ambient conditions (i.e., it is open to the atmosphere) or contacts some other form of wound dressing.

The first layer and the second layer may contain the same or different polymeric materials. An adhesive may optionally be used to bond the first layer to the second layer. In some embodiments, the first layer and/or the second layer is a polymeric material that may be a thermoplastic material or a thermosetting material. The thermosetting material is crosslinkable and can be crosslinked using thermal energy and/or irradiation. Irradiation may include ultraviolet light, infrared radiation, microwave radiation, xrays, electron beam radiation, proton or neutron beam radiation, or a combination thereof. The crosslinked materials can be highly crosslinked or lightly crosslinked in the form of gels.

The polymeric material may include oligomers, homopolymers, a blend or oligomers and/or homopolymers, copolymers, ionomers, polyelectrolytes, dendrimers, or a combination thereof. Copolymers can include block copolymers, random copolymers, gradient copolymers, alternating copolymers, star block copolymers, or combinations thereof.

Example of polymers (both thermoplastic or thermosetting) that may be used in either the first layer and/or the second layer are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination thereof.

Examples of polyelectrolytes include polystyrene sulfonic acid, polyacrylic acid, pectin, carageenan, alginates, carboxymethylcellulose, polyvinylpyrrolidone, or the like, or a combination thereof.

Examples of thermosetting polymers include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination thereof.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleic anhydride/acrylonitrile-butadiene-styrene, polyether etherketone/polyethersulfone, polyether etherketone/polyetherimide polyethylene/nylon, polyethylene/polyacetal, or the like.

In some embodiments, the first layer is a biodegradable gel formed of a biodegradable polymeric material. In an embodiment, the first layer and/or the second layer may be thermoplastic layers, biodegradable layers and/or biocompatible layers and may comprise any of the polymers described herein. In an embodiment, the first layer and/or the second layer may be thermosetting layers, biodegradable layers and/or biocompatible layers. The thermoplastic or thermosetting materials used herein may be biodegradable layers and/or biocompatible layers. Examples of the biodegradable polymeric material used to form the first layer include, but are not limited to, any of the biodegradable polymers described herein. In an embodiment, the first layer comprises a gel formed by at least one natural or synthetic biodegradable polymer. In another embodiment, the first layer is formed by at least one synthetic biodegradable polymer and the first layer and the at least one synthetic biodegradable polymer do not include a gelatin, collagen, a CAPGEL™ gel, a copper capillary alginate gels (CCAG) or and/or a natural biodegradable polymer. In an exemplary embodiment, the first layer is a biodegradable hydrogel. In another exemplary embodiment, the first layer and the second layer are biodegradable hydrogels.

Referring to FIG. 1, a schematic diagram of an embodiment of the multilayered wound dressing is shown. The multilayered wound dressing 100 comprises a first layer 110 (also referred to herein as a "scaffold") which serves as a dermal template by accelerating neovascularization of a wound and has a three-dimensional microchannel architecture. The multilayered wound dressing 100 further comprises a second layer 120 that directly contacts the first layer and facilitates autologous epidermal healing via guided cell migration by virtue of directional texturing 130 that is disposed on this second layer, as described further herein.

The first layer generally has a plurality of channels that facilitate neovascularization while the texturing on the second layer facilitate directional cell growth in the wound dressing. the channels are pathways that have diameters on the order of nanometers to micrometers.

In an embodiment, the second layer has the same chemical composition as the first layer. Neither the first layer nor the second layer is a gel. The first layer and the second layer may be thermoplastic layers, biodegradable layers and/or biocompatible layers and may comprise any of the non-gel polymers described herein. Since the first layer and the second layer are compositionally the same, no intermediate or reacting layer is needed to bond the first layer with the second layer. The first layer and/or second layer may be a crosslinked layer.

In an embodiment, the wound dressing is customizable to a particular patient's wound. An image such as a computed tomography ("CT") scan is used to generate a three-dimensional computer model of the patient's anatomy in the location of the wound, including the microscale ridges and projections which make up the dermal/epidermal junction of the patient's skin in the location where the wound is located. Using the computer model, a surface 140 of the first layer opposite the surface that is directly in contact with the second layer is textured with a texture that is complementary to a patient's dermal/epidermal anatomy where the wound is located. The resulting texture on the first layer utilizes the physical guidance cues to accelerate coverage of the wound with keratinocytes, thereby further accelerating the healing process for the wound. The first layer consists of the 3D capillary structure and will be used to promote dermal healing and/or neovascularization. The customized first layer having such a texture thus further facilitates autologous dermal healing via guided cell migration.

In an embodiment, a method comprises forming a first layer of a polymeric material; forming a second layer of the same polymeric material as the first layer on the first layer; and forming a textured surface of the second layer of the same polymeric material as the first layer, the textured surface being operative to facilitate directional cell growth when used in a wound dressing, wherein the first layer and the second layer are formed using an additive manufacturing process.

In another embodiment, the method further comprises generating a three-dimensional computer model of an anatomy of a patient's epidermis where a wound is located; and forming a textured surface of the second layer of the same polymeric material as the first layer, the textured surface being complementary to the three-dimensional computer model. The second layer is the layer that contacts the epidermis of the patient.

The layers of the multilayered wound dressing and the respective textured surfaces thereof, are each formed using the same material and together are formed as a single piece using an additive manufacturing process. In an embodiment, the multilayered wound dressing is formed as three-dimensional object using a three-dimensional ("3D") printing additive manufacturing process. In a 3D printing additive manufacturing process, successive layers of material are formed under computer control to create a three-dimensional object based on a three-dimensional computer model. The three-dimensional computer model may be created using a computer aided design ("CAD") package, a 3D scanner or by a plain digital camera and photogrammetry software.

In one embodiment, any technique suitable for 3D printing may be employed, including but not limited to, extrusion or fused deposition and sintering-based processes using a powdered material(s). In an embodiment, fused deposition modeling is used to produce the three-dimensional object by extruding small beads of material which harden to form layers. In another embodiment, materials in a granular bed are selectively fused. This technique fuses parts of the layer and then moves downward in the working area, adding another layer of granules and repeating the process until the piece has built up to completion. The process uses the unfused media to support overhangs and thin walls in the part being produced, which reduces the need for temporary auxiliary supports for the piece. A laser may then be used to sinter the media into a solid.

In another embodiment, any technique suitable for 3D printing may be employed, including but not limited to, stereolithography, bio-printing, extrusion or fused deposition and sintering-based processes using a powdered material(s). In an exemplary embodiment, stereolithography or bio-printing inkjet 3D printing processes are employed.

In another embodiment, fused deposition modeling is used to produce the three-dimensional object by extruding small beads of material which harden to form layers. In another embodiment, materials in a granular bed are selectively fused. This technique fuses parts of the layer and then moves downward in the working area, adding another layer of granules and repeating the process until the piece has built up to completion. The process uses the unfused media to support overhangs and thin walls in the part being produced, which reduces the need for temporary auxiliary supports for the piece. A laser may then be used to sinter the media into a solid.

In another embodiment, the three-dimensional object is produced via an inkjet 3D printing system. The printer creates the three-dimensional object one layer at a time by spreading a layer of powder and printing a binder in the cross-section of the part using an inkjet-like process. This process is repeated until every layer has been printed. Successive layers of material are thus formed to build the first and second respective layers of the multilayered wound dressing and the respective surfaces thereof. Similarly, the successive layers of material are built to form the microchannel architecture of the first layer.

In an embodiment, the wound dressing is customizable to a particular patient's wound. An image such as a computed tomography ("CT") scan is used to generate a three-dimensional computer model of the patient's anatomy in the location of the wound. Using the computer model, a surface 140 of the first layer opposite the surface that is directly in contact with the second layer is created with a size and geometry that is complementary to a patient's anatomy where the wound is located. The resulting texture on the second layer utilizes the physical guidance cues to accelerate coverage of the wound with keratinocytes, thereby further accelerating the healing process for the wound. The customized first layer having such a texture thus further facilitates autologous epidermal healing via guided cell migration.

In another embodiment, the first layer functions as a "scaffold" and serves as a dermal template by accelerating neovascularization and is manufactured from a gel. An exemplary gel is CAPGEL™ described in detail in U.S. Pat. No. 7,601,525. The second layer may or may not contact the first layer directly and facilitates autologous epidermal healing via guided cell migration by virtue of directional texturing that is disposed on this layer. The multilayered wound dressing may comprise three, four, five or more layers if desired. In one exemplary embodiment, the first layer and the second layer may both comprise the same gel. In another exemplary embodiment, the first and the second layers may be compositionally different from each other.

In an embodiment, the first layer may comprise a plurality of layers—i.e., the first layer may comprise 2 or more primary layers, 3 or more primary layers, 4 or more primary layers and so on. The plurality of layers of the first layer are termed primary layers. Thus a first layer may comprise three primary layers—a first primary layer that contacts the second layer on a first surface while contacting a second primary layer on a second surface that is opposed to the first surface, where the second primary layer contacts a third primary layer on a surface that is opposed to the surface that contacts the first primary layer. This plurality of layers may be manufactured by additive manufacturing.

The layers may have a gradually varying physical structure—for example, the channels in the first primary layer may have a larger cross-sectional area than those channels in the second primary layer while those in the second primary layer may have a larger cross-sectional area than those channels in the third primary layer, and so on.

In another embodiment, the layers of the first layer may have a gradually varying chemistry—the first primary layer may have a higher crosslink density than the second primary layer which has a higher crosslink density than the third primary layer.

In one embodiment, the first layer comprises a crosslinked polymeric gel while the second layer comprises a crosslinked polymeric gel. Both crosslinked polymeric gels are biocompatible and biodegradable. Biocompatible polymers are those which can be inserted in the body of a living being without any undesirable side effects. The biodegradable polymers upon undergoing degradation can be consumed by the body without any undesirable side effects. In another embodiment, the first layer comprises a crosslinked polymeric gel while the second layer comprises a thermoplastic polymer. It is desirable for the first layer and the second layer to be covalently or ionically bonded together. The first layer generally has channels that facilitate neovascularization while the texturing on the second layer facilitate directional cell growth in the wound healing dressing.

The first layer generally comprises a biodegradable gel. The gels used in the first layer are copper capillary alginate gels (CCAG) stabilized in a fluid and biological environment. In one embodiment, the CCAG are stabilized via cross-linking with at least one carbodiimide. In a preferred embodiment, stabilization involves exchanging ions with a cation, preferably barium, forming a polyelectrolyte laminate complex (PEC) by adding chitosan, or oligochitosan, or a combination of both. In an embodiment, the first layer may comprise a plurality of gel sublayers. The first layer may comprise two or more, three or more, or five or more gel layers.

In another preferred embodiment, the first layer comprises a copolymer of polyurethane and polylactic acid or a copolymer of polyurethane and polylactic-glycolic acid.

In one embodiment, details of manufacturing of the first layer are provided in Gelatinized Copper—Capillary Alginate Gel Functions as an Injectable Tissue Scaffolding System for Stem Cell Transplants to Willenberg et al., published in the Journal of Biomaterials Science 22 (2011) 1621-1637, the entire contents of which are hereby incorporated by reference.

The gels are useful as biomaterial scaffolds to provide a structure useful for containing, growing, and/or regenerating biological agents for subsequent in vivo implantation in humans or animals. One aspect of the present invention is directed to a modified or stabilized CCAG, which may be used in the first layer. CCAG comprises a soft hydrogel having a continuous parallel microtubular architecture. Beneficially, the stabilized CCAG can impose structural order on growing and regenerating cells and tissues. The microtubular or capillary diameter (also called micropores) can range from about 3 μm (micrometers) to about 300 μm. Preferably, the capillary diameter is within the range of about 10 μm to about 250 μm. More preferably, the capillary diameter is within about 25 μm to about 30 μm.

Advantageously, the cell morphology can be designed to promote efficient cell growth. The skilled artisan would understand that cells behave differently at different curved surfaces. For example, the cells might propagate and/or proliferate differently. Morphology can be adjusted to the desired shape via freeze drying techniques.

Capillary diameter can vary at different gel levels because it is a function of gel thickness. Other physical properties of the subject scaffolds also vary with gel thickness. For example, capillary density decreases as parent gel thickness increases, wherein a parent gel refers to the initially grown raw CCAG from which samples are derived to make a stabilized first layer. The average surface area also decreases as parent gel thickness increases.

Advantageously, a stabilized CCAG possesses superior properties over a CCAG alone when utilized in a fluid environment. The stabilized CCAG experiences a decrease in swelling and greater maintenance of mechanical properties. The stabilized gel's structure, positive surface charge and hydrophilic character are useful for preparing scaffolds for growth and regeneration of multiple cell types. The stabilizing agent can be selected from a variety of compounds and ions. The key is for the stabilizing agent to be non-toxic to a growing cell or its surrounding environment or to be bound to the alginate gel in such a way that it will not be released into the surrounding physiological environment. Examples can include, without limitation, cations, polysaccharides and carbodiimides. Preferably, the cations are divalent cations. More preferably, the divalent cation is a barium ion. Barium ion is an example of an agent that is toxic to cells. However, it remains bound to the alginate gel in physiological environment, thus negating its toxicity. Any divalent ions can be used. Calcium and barium may also be used to stabilize gels.

Preferably, the polysaccharide is chitosan or oligochitosan. Preferably, the carbodiimide is selected from N-ethyl-N'-(3-dimethylaminopropyl)-carbodiimide, NN'-dicyclohexyl-carbodiimide (DCC), N'-diisopropyl-carbodiimide, N'N'-di-tert-butylcarbodiimide 1-cyclo-hexyl-3-(4-diethylaminocyclohexyl)carbodiimide, 1,3-di-(4-diethylaminocyclo-hexyl)carbodiimide, 1-cyclohexyl-3-(-diethylaminoethylcarbodiimide, and 1-cyclohexyl-1-cyclohexyl-3-(2-morphonlinyl-(4)-ethyl)carbodiimide 1-cyclohexyl-3-(4-diethyl-aminocyclohexyl)carbodiimide. Also, because the scaffolds comprise potentially edible components, they are useful as the basis for synthetic meat products that grow and regenerate animal cells. In contrast, the CCAG alone dissolves in cell culture environments, and copper ions leach out and infiltrate the surrounding environment.

The gel functions as a biomaterial scaffold, which is non-toxic to a cell in vivo or in vitro, wherein the scaffold comprises an alginate gel and at least one stabilizing agent; wherein the gel further comprises a plurality of continuous microtubular copper channels. While this disclosure discusses copper channels, metals other than copper may also be used. The compositions (e.g., stabilized gel scaffolds or stabilized gel first layers) of the present invention can be used as a vehicle for the in situ delivery of biologically active agents. The biologically active agents incorporated into, or included as an additive within, the composition of the present invention can include, without limitation, medicaments, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composition into a patient and to promote subsequent integration and healing processes. The active agents include, but are not limited to, antibodies, antibody fragments, antibiotics, antifungal agents, antibacterial agents, anti-viral agents, anti-parasitic agents, growth factors, neurotrophic factors, angiogenic factors, anaesthetics, mucopolysaccharides, metals, cells, proteins, polynucleotides, polypeptides enzymes, degradation agents, lipids, carbohydrates, chemical compounds such as pharmaceuticals and other wound healing agents. The substances can be therapeutic agents, diagnostic materials, and/or research reagents.

Examples of proteins that may be incorporated into or otherwise associated with the composition are collagen (of the various types) and fibronectin. The composition can be adapted to allow delayed release of the biologically active agents, or controlled release over time.

After processing the compositions of the present invention, live cells can be subsequently allowed to infiltrate the composition through tissue engineering techniques. Advantageously, the parallel microtubular architecture of the scaffold (e.g., conduit) of the invention facilitates tissue ingrowth and may be infiltrated with nutrient and/or cellular material at the implant site or in cell cultures. Nutrients may also diffuse across the stabilized CCAG to nourish cells seeded within the copper channels.

As indicated above, cells can be seeded onto and/or within the copper channels of the alginate gels of the present invention. Likewise, tissues such as cartilage or nerve tissue can be associated with the gels prior to implantation within a patient. The cells utilized may include those cells arising from the ectoderm, mesoderm, or endoderm germ cell layers. Examples of cells include, but are not limited to, pancreatic islet cells, bone cells (such as osteoclasts, osteoblasts, chondrocytes, and osteocytes), blood cells, marrow cells, epithelial cells, neural cells (e.g., neurons, astrocytes, and oligodendrocytes), muscle cells, adipocytes, tendon cells, ligament cells, dermal cells, fibroblasts, and dental cells (odontoblasts and ameloblasts). Seeded cells can be autogenic, allogenic, or xenogenic to the patient in which the scaffold is implanted. Seeded cells can be encapsulated or non-encapsulated. The cells can be stem cells or progenitor cells (such as stem cells or progenitor cells of any of the aforementioned differentiated cell types), or mature, differentiated cells. For example, the cells seeded onto and/or within the alginate gels can be hematopoietic stem cells, mesenchymal stem cells, neural stem cells, or others. The stem cells, progenitor cells, or mature cells can be genetically modified or non-genetically modified.

As used herein, the term "cell" is intended to include primary cells, cells of cell culture, and cells of cell lines (e.g., cells of tumors or immortalized cells), unless otherwise specified. As will be understood by one of skill in the art, there are over 200 cell types in the human body. The methods and compositions of the present invention may utilize any of these cell types, singly or in combination. Other cells suitable for use with the compositions and methods of the present invention include those disclosed by Spier R. E. et al., eds., *The Encyclopedia of Cell Technology* (2000), John Wiley & Sons, Inc., and Alberts B. et al., eds., *Molecular Biology of the Cell* (1994), 3$^{rd}$ ed., Garland Publishing, Inc., e.g., pages 1188-1189, which are incorporated herein by reference in their entireties.

One embodiment of the present invention is a negatively charged CCAG first layer. Preferably, barium ions stabilize the CCAG by additional cross-linking with the alginate within and throughout the scaffold, although other ions may be used, for example, $Cd^{2+}$, $Cu^{2+}$, $Ca^{2+}$, $Ni^{2+}$, $Co^{2+}$, and $Mn^{2+}$. Advantageously, the pore morphology of the barium-stabilized scaffold is round when placed in fluid environment. Another embodiment of the invention is a positively charged CCAG scaffold. In another specific embodiment, oligochitosan is used to stabilize the CCAG. The oligochitosan and alginate gel react to form a cross-linked skin surrounding an inner core of CCAG.

In yet another embodiment, both an ion exchange with cations like barium and a reaction with at least one electrostatic moiety, which form a polyelectrolyte complex (PEC), are utilized in stabilizing the CCAG scaffold. These moieties can include, without limitation, chitosan, its derivatives, oligochitosan, poly-lysine, carbodiimides, and ethylene diamine Other cations, for example, $Cd^{2+}$, $Cu^{2+}$, $Ca^{2+}$, $Ni^{2+}$, $Co^{2+}$, and $Mn^{2+}$, may also be used. Advantageously, cells adhere, spread and proliferate on positively charged chitosan surfaces. Also, the PEC stabilized scaffolds can be prepared with multiple PEC layers. Preferably, there are three to five layers of PEC. The advantages of multiple layered CCAG are increased mechanical integrity and, if used as a carrier for drugs, greater flexibility in controlling diffusion rates.

Methods of preparing of CCAG are well known in the art, for example, as disclosed by Hassan et al., Journal of Polymer Science, 1991, 29(11):1645; European Polymer Journal, 1988, 24(12):1173; Thiele, H. Histolyse und Histogenese, Gewebe und ionotrope Gele, Prinzip einer Stukturbildung, 1967, Frankfurt: Akademische Verlagsgesellschaft; Schuberth, R. Ionotropic Copper Alginates: Investigations into the formation of capillary gels and filtering properties of the primary membrane, 1992, University of Regensburg: Regensburg.

The base alginate may be derived from brown sea algae. The alginate can be derived from, for example and without limitation, *Laminaria hyperborea* or *Macrocystis pyrifera*.

The method of preparing a barium stabilized copper capillary gel comprises initially washing CCAG in deionized (DI) water for a sufficient period of time to remove excess, unreacted copper ions, submerging CCAG in a aqueous barium solution while agitating, and washing the resulting scaffold. Preferably, the barium solution is $Ba(OH)_2$. The concentration of the $Ba(OH)_2$ solution varies from about 0.01 M to about 0.1 M and is preferably about 0.05M $Ba(OH)_2$. The submerging step lasts for a period of time sufficient for the $Ba^{2+}$ ions to diffuse across the CCAG. The diffusion is measurable by observing the gel color change from a light blue-green to a deep blue. Preferably, the submerging step takes place within about 12 to about 48 hours. More preferably, the submerging step takes place within about 12 to about 24 hours. Optionally, the barium solution can be completely exchanged at periodic intervals. Preferably, a fresh solution of about 0.05M $Ba(OH)_2$ is exchanged with the spent solution about every twelve hours. The final washing step occurs in a DI water bath, a physiologically balanced salt solution wash, or both. These steps are conducted at temperatures that vary between about 13° C. and about 33° C. Preferably, the steps take place at room temperature (around 23° C.). Poorly washed samples have exhibited black layers within the gel.

The first layer may also comprise chitosan-stabilized CCAG. Chitosan is a natural polysaccharide prepared from crustacean cells, which is known to possess many beneficial properties, such as biocompatibility, wound-healing properties, and anti-microbial properties (Otterlei, M. et al. Vaccine, 1994, 12:825-32; Muzzarelli, R. et al. Biomaterials, 1988, 10:598-603; Pappineau, A. M. et al. Food Biotechnol, 1991, 5:45-47; Erbacher, P. et al. Pharm Res, 1998, 15:1332-9; Richardson, S. C. et al. Int J Pharm, 1999, 178:231-43). Oligochitosan is a small chained, thus a low molecular weight, chitosan. Advantageously, oligochitosan is water soluble at a neutral pH.

The term "chitosan", as used herein, will be understood by those skilled in the art to include all derivatives of chitin, or poly-N-aceryl-D-glucosamine (including all polyglucosamine and oligomers of glucosamine materials of different molecular weights), in which the greater proportion of the N-acetyl groups have been removed through hydrolysis. Generally, chitosans are a family of cationic, binary heteropolysaccharides composed of (1→4)-linked 2-acetamido-2-deoxy-β-D-glucose (GlcNAc, A-unit) and 2-amino-2-deoxy-β-D-glucose, (GlcN; D-unit) (Varum K. M. et al., *Carbohydr. Res.*, 1991, 217:19-27; Sannan T. et al., *Macromol. Chem.*, 1776, 177:3589-3600). Preferably, the chitosan has a positive charge. Chitosan, chitosan derivatives or salts (e.g., nitrate, phosphate, sulphate, hydrochloride, glutamate, lactate or acetate salts) of chitosan may be used and are included within the meaning of the term "chitosin". As used herein, the term "chitosan derivatives" are intended to include ester, ether or other derivatives formed by bonding of acyl and/or alkyl groups with OH groups, but not the $NH_2$ groups, of chitosan. Examples are O-alkyl ethers of chitosan and O-acyl esters of chitosan. Modified chitosans, particularly those conjugated to polyethylene glycol, are included in this definition. Low and medium viscosity chitosans (for example CL113, G210 and CL110) may be obtained from various sources, including PRONOVA Biopolymer, Ltd. (UK); SEIGAGAKU America Inc. (Maryland, USA); MERON (India) Pvt, Ltd. (India); VANSON Ltd. (Virginia, USA); and AMS Biotechnology Ltd. (UK). Suitable derivatives include those which are disclosed in Roberts, Chitin Chemistry, MacMillan Press Ltd., London (1992). Optimization of structural variables such as the charge density and molecular weight of the chitosan for efficiency of delivery of biologically active agents is contemplated and encompassed by the present invention.

The chitosan (or chitosan derivative or salt) preferably used has a molecular weight of 1,000 Dalton or more, preferably in the range 1,000 to 4,000 Dalton. Chitosans of different low molecular weights can be prepared by enzymatic degradation of chitosan using chitosanase or by the addition of nitrous acid. Both procedures are well known to those skilled in the art and are described in various publications (Li et al., *Plant Physiol. Biochem.*, 1995, 33:599-603; Allan and Peyron, *Carbohydrate Research*, 1995, 277: 257-272; Damard and Cartier, *Int. J. Biol. Macromol.*, 1989, 11:297-302). Preferably, the chitosan is water-soluble and may be produced from chitin by deacetylation to a degree of greater than 40%, preferably between 50% and 98%, and more preferably between 70% and 90%.

One method of preparing a chitosan-stabilized CCAG comprises, washing the CCAG in a deionized (DI) water bath to remove any excess copper ions, contacting a chitosan solution with the CCAG by flowing the solution through the microtubular structure through the CCAG, and washing the resulting stabilized scaffold in a solution to remove any unbonded or excess chitosan. One washing step can be omitted. The concentration of the chitosan solution can vary between about 0.1 w/v % and about 3 w/v %. Preferably, the concentration of the chitosan solution is about 0.2 w/v % to about 2 w/v %. More preferably, the concentration of the solution is about 2 w/v %. Advantageously, the solvent of the solution can be water or acetic acid.

Optionally, the contacting and second washing steps can be repeated alternating alginate and chitosan or oligochitosan solutions to produce multi-layers of PEC on the scaffold. Preferably, the contacting and second washing steps are repeated about three to five times to produce three to five layered CCAG. In other words, the first layer may comprise two or more layers of gel that contain channels that facilitate neovascularization One method of preparing a CCAG first layer stabilized by both barium and chitosan involves washing raw CCAG in DI water for a sufficient period of time to remove excess, unreacted copper ions, submerging CCAG in an aqueous barium solution while agitating, washing the resulting scaffold, contacting a chitosan solution with the barium-stabilized CCAG, and a third washing to remove any unbound or excess chitosan. Again, one or two of the washing steps may be omitted.

The second layer may comprise a biodegradable gel similar in composition to that of the first layer. Biodegradable gels can be comprised of natural polymers, i.e., gelatin or collagen or synthetic non-natural polymers. Examples of synthetic biodegradable hydrogels include polyethylene glycol (PEG) block copolymers that include polylactic acid (PLA), polyglycolic acid (PGA), polycaprolactone (PCL) or combinations of these. The second layer may also comprise hydrogels crosslinked with enzyme-degradable peptide sequences degradable by cellular secretions such as matrix metalloproteinases (MMPs). MMP-2 and MMP-9 are prevalent in the wound environment. In another embodiment, the second layer may comprise a biodegradable thermoplastic material that is capable of being reacted ionically or covalently with the first layer. In yet another embodiment the second layer is compatible with the first layer and requires no chemical reactive bonding.

Suitable examples of thermoplastic biodegradable polymers are as polylactic-glycolic acid (PLGA), copolymers of polyurethane and polylactic-glycolic acid, polyurethanes, poly-caprolactone (PCL), copolymers of polylactic-glycolic acid and poly-caprolactone (PCL-PLGA copolymer), poly-hydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), or the like, or combinations comprising at least one of the foregoing biodegradable polymers. These polymers can be surface treated to facilitate covalent or ionic bonding with the gelatin layer. This may involve surface treating the thermoplastic biodegradable material with ionizing radiation, electron beam radiation, xray radiation or with strong acids (hydrochloric acid, nitric acid, sulfuric acid, and the like) to contain reactive groups such as primary amines and carboxylic acids.

Other thermoplastic polymers which are biocompatible but not biodegradable may also be used. Examples include polytetrafluoroethylene or polyorganosiloxanes. Preferred polymers for the first and second layer are the biodegradable polymers listed above.

The second layer has a texture disposed on at least one surface. The textured surface of the second layer does not contact the first layer. The texturing facilitates cell growth along particular directions determined by the orientation of the texture.

The second layer may have any kind of texture. Examples of surface texture are detailed in US 20050003146 A1 to Spath, U.S. Pat. No. 7,143,709 B2 to Brennan et al., and patent application having Ser. No. 12/550,870 to Brennan et al., the entire contents of which are hereby incorporated by reference in their entirety.

At least one surface of the second layer comprises a plurality of spaced features; the features arranged in a plurality of groupings; the groupings of features being arranged with respect to one another so as to define a tortuous pathway when viewed in a first direction. When viewed in a second direction, the groupings of features are arranged to define a linear pathway. Radial patterns may also be used. In radial patterns the patterns emanate from a focal point and spread outwards in a radial direction.

In one embodiment, when viewed in a second direction, the pathway between the features may be non-linear and non-sinusoidal. In other words, the pathway can be non-linear and aperiodic. In another embodiment, the pathway between the features may be linear but of a varying thickness. The plurality of spaced features may be projected outwards from a surface or projected into the surface. In one embodiment, the plurality of spaced features may have the same chemical composition as the surface. In another embodiment, the plurality of spaced features may have a different chemical composition from the surface.

The plurality of features each have at least one microscale (micrometer or nanometer sized) dimension and has at least one neighboring feature having a substantially different geometry. The average first feature spacing between the adjacent features is between 10 nanometers to 100 micrometers in at least a portion of the surface, wherein said plurality of spaced apart features are represented by a periodic function. In one embodiment, the first feature spacing is between 0.5 micrometers ($\mu m$) and 5 $\mu m$ in at least a portion of the surface. In another embodiment, the first feature spacing is between 15 and 60 $\mu m$ in at least a portion of said surface. As noted above, the periodic function comprises two different sinusoidal waves. In one embodiment, the topography resembles the topography of sharkskin (e.g., the Sharklet microtopography). In another embodiment, the pattern comprises at least one multi-element plateau layer disposed on a portion of the surface, wherein a spacing distance between elements of the plateau layer provides a second feature spacing; the second feature spacing being substantially different when compared to said first feature spacing. It is to be noted that each of the features of the plurality of features are separated from each other and do not contact one another.

The pattern of the texture is separated from a neighboring pattern by a tortuous pathway. The tortuous pathway may be represented by a periodic function. The periodic functions may be different for each tortuous pathway. In one embodiment, the patterns can be separated from one another by tortuous pathways that can be represented by two or more periodic functions. The periodic functions may comprise a sinusoidal wave. In an exemplary embodiment, the periodic function may comprise two or more sinusoidal waves.

In another embodiment, when a plurality of different tortuous pathways are represented by a plurality of periodic functions respectively, the respective periodic functions may be separated by a fixed phase difference. In yet another embodiment, when a plurality of different tortuous pathways are represented by a plurality of periodic functions respectively, the respective periodic functions may be separated by a variable phase difference.

In one embodiment, the plurality of spaced apart features have a substantially planar top surface. In another embodiment, a multi-element plateau layer can be disposed on a portion of the surface, wherein a spacing distance between elements of said plateau layer provide a second feature spacing; the second feature spacing being substantially different when compared to the first feature spacing.

In one embodiment, a sum of a number of features shared by two neighboring groupings is equal to an odd number. In another embodiment, a sum of a number of features shared by two neighboring groupings is equal to an even number. Details of the texture (in the form of Figures may be seen in the patent application having Ser. No. 12/550,870 to Brennan et al., the entire contents of which are hereby incorporated by reference in their entirety.

In one embodiment, in one method of manufacturing the multilayered wound dressing, a precursor sol that can be converted into a gel is first disposed in a mold. The gel is preferably gelatin. The precursor sol contains precursors that produce the aforementioned gel upon being initially cured. The initial curing step partially cures the sol to produce a gel. Initial crosslink of the gelatin is conducted with a solution of EDC (scientific name: N-(3-Dimethylaminopropyl)-N'-ethylcarbodiimide hydrochloride) and NHS (scientific name: N-hydroxysuccinimide).

The mold walls contain the desired surface texture and impart the texture at least one surface of the gel when it initially cured. During the molding, the temperature of the mold and the pressure in the mold may be increased to impart strength to the gel. The temperature constraints appear to be very sensitive to avoid bubbles/disruptions of the pattern. The temperatures/pH involved in the process are also within the realm of physiological temperature, which we believe may allow the incorporation of additional biologically active proteins/molecules.

Upon being disposed in the mold, the sol is subjected to curing to form a gel having one or more surfaces that are textured. This layer with the texture is the second layer. In an embodiment, two or more surfaces may be textured. In another embodiment, three or more surfaces may be textured. In another embodiment, all surfaces may be textured including the surface that contacts the first layer. Texturing of the surface that contacts the first layer may facilitate and improve mechanical adhesion between the first and the second layer without the use of covalent or ionic bonding.

As noted above, the second layer does not have to comprise the gel. It may be manufactured from thermoplastic biodegradable polymers and in this particular case, no curing of the second layer is desirable.

In another embodiment, in another method of manufacturing the second layer, beads of the gel are first manufactured by extruding the gel through a capillary device or a syringe fitted with a needle. The beads have the internal channels disclosed above. The gel is extruded into a mold that contains a texture. The gel does not have to be in the form of beads. It can comprise irregular shaped portions of the gel. The texture is transferred to the gel surface to form the second layer.

After texturing and initially curing the second layer, a thin liquid layer of the sol is disposed on the initially cured gel (the second layer) to facilitate bonding of the second layer with a first layer. Following this another initially cured layer of gel (the first layer) may manufactured as disclosed above and then disposed on the second layer. The second layer is then bonded to the first layer using the liquid layer of sol. The surfaces of the first layer are generally untextured but can be textured if desired.

The first and second layer now in contact with each other may be bonded together using another EDC/NHS solution to form a solid bilayer device. The solid bilayer device may be used as a wound dressing.

In one embodiment, the multilayer device may be disposed in or on a wound. Cells will begin to grow in the micropores in the first layer and along the surface texture provided by the texturing in the second layer. Since one or more layers in the multilayer wound dressing are biodegradable, the orientation of the pores and the channels facilitates the development of initial cell growth and these initial cells further serve as templates for further cell growth as the biodegradable materials begin to disintegrate.

By having a plurality of different layers having a different micropore orientation in each layer, a plurality of cell layers may be obtained each of which have a different orientation making the healed region significantly stronger than it was prior to the wound occurring. In addition, by selecting different aspect ratios for the texture as well as for the micropores in the various layers, the aspect ratio of the new cells can also be varied to improve the healing process.

The different kinds of cells may be selected from the group consisting of embryonic stem cells, adult stem cells, blast cells, cloned cells, fertilized ova, placental cells, keratinocytes, basal epidermal cells, hair shaft cells, hair-root sheath cells, surface epithelial cells, basal epithelial cells, urinary epithelial cells, salivary gland cells, mucous cells, serous cells, von Ebner's gland cells, mammary gland cells, lacrimal gland cells, ceruminous gland cells, eccrine sweat gland cells, apocrine sweat gland cells, Moll gland cells, sebaceous gland cells, Bowman's gland cells, Brunner's gland cells, seminal vesicle cells, prostate gland cells, bulbourethral gland cells, Bartholin's gland cells, Littré gland cells, uterine endometrial cells, goblet cells of the respiratory or digestive tracts, mucous cells of the stomach, zymogenic cells of the gastric gland, oxyntic cells of the gastric gland, insulin-producing 13 cells, glucagon-producing a cells, somatostatin-producing 6 cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peripolar cells of the kidney, mesangial cells of the kidney, brush border cells of the intestine, striated duct cells of exocrine glands, gall bladder epithelial cells, brush border cells of the proximal tubule of the kidney, distal tubule cells of the kidney, nonciliated cells of ductulus efferens, epididymal principal cells, epididymal basal cells, hepatocytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroids plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood channels, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, megakaryocytes, monocytes, connective tissue macrophages, Langerhans cells, osteoclasts, dendritic cells, microglial cells, neutrophils, eosinophils, basophils, mast cells, plasma cells, helper T cells, suppressor T cells, killer T cells, immunoglobulin M, immunoglobulin G, immunoglobulin A, immunoglobulin E, killer cells, rod cells, cone cells, inner hair cells of the organ of Corti, outer hair cells of the organ of Corti, type I hair cells of the vestibular apparatus of the ear, type II cells of the vestibular apparatus of the ear, type II taste bud cells, olfactory neurons, basal cells of olfactory epithelium, type I carotid body cells, type Ii carotid body cells, Merkel cells, primary sensory neurons specialized for touch, primary sensory neurons specialized for temperature, primary neurons specialized for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, oogonium, oocytes, spermatocytes, spermatogonium, ovarian follicle cells, Sertoli cells, and thymus epithelial cells, or combinations thereof.

The bilayer device and the method of manufacturing is disclosed in the following non-limiting examples.

Example 1

Smooth (SM) and micropatterned (+1.7SK2×2) samples were fabricated by casting polydimethylsiloxane elastomer (Xiameter RTV-4232-T2, Dow Corning; PDMSe) against negative silicon wafer molds. Circular samples (d=20 mm) were adhered to a 12-well plate with features aligned parallel to the direction of cell migration and treated with fibronectin (15 μg/mL overnight) to facilitate cell attachment. SM PDMSe rectangles (5 mm×20 mm) were placed along the center of the sample to create a modified scratch assay. Human epidermal keratinocytes (HEKs) were seeded over the entire configuration at 1×10$^4$ cells/cm$^2$ and maintained in complete keratinocyte growth media (dermal cell basal medium, 0.4% bovine pituitary extract, 0.5 ng/ml rh TGF-alpha, 6 mM L-glutamine, 100 ng/ml hydrocortisone, 5 μg/ml insulin, 1 μM epinephrine, 5 μg/ml apo-transferrin, 50 U/ml penicillin/streptomyocin and 1 μg/ml Fungizone antimycotic). At ~70% confluence, PDMSe rectangles were removed to allow cell migration across the empty patterned area. Migration was monitored via light microscopy until Day 7 when samples were stained with CellTracker Orange and fixed. Fluorescent microscopy images were taken of the wounded area and the average area covered by cells within this region was calculated using ImageJ software.

The nomenclature adopted here (e.g., +1.7SK2×2) should deciphered as follows: The +1.7 indicates the height of the texture above the base surface while the SK refers to a Sharklet pattern depicted and described in U.S. Pat. No. 7,143,709 B2 to Brennan et al., and patent application having Ser. No. 12/550,870 to Brennan et al. A negative sign (–) preceding the 1.7 would indicate that the texture is below the base surface. The first 2 in SK2×2 stands for the width of each feature in the pattern while the second 2 stands for the spacing between the features in the pattern.

Figure 2:
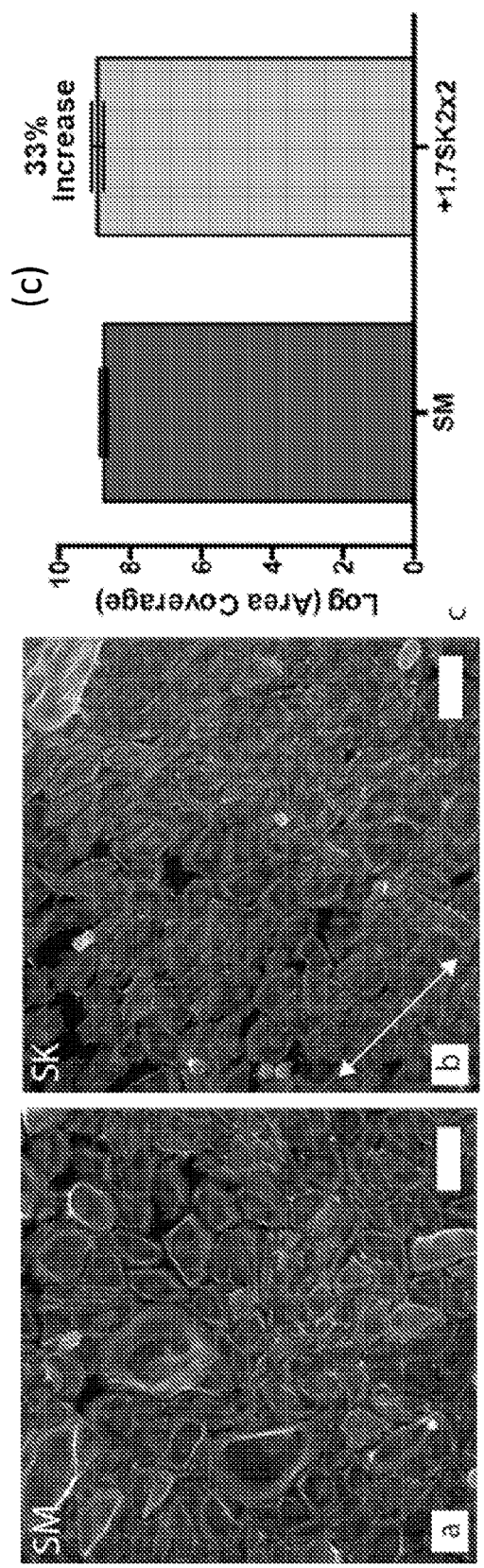
FIG. 2 shows a) and b) HEKs cultured on SM (smooth) and SK (+1.7SK2×2) (Sharklet) surfaces, stained for actin (white) and nuclei (blue). Staining reveals contact guidance on SK (arrow indicates pattern direction). Scale bars, 50 µm. c) results of a modified scratch wound assay show 33% greater coverage of cells within the wounded area after 3d on SK versus SM.

Sharklet micropatterns (Table 1) have been designed on two size scales (e.g., 5-μm and 50-μm spacings) based on previously reported results, which demonstrated that channels of these sizes enhanced re-epithelialization and recapitulated the texture of the native epidermal-dermal junction. Various aspect ratios (i.e., ratio of topography height to topography width) will allow us to optimize microtopography height for guiding cell migration and neo-tissue formation. FIG. 2 shows. a) and b) HEKs cultured on SM (smooth) and SK (Sharklet, +1.7SK2×2) surfaces, stained for actin (white) and nuclei (blue). Staining reveals contact guidance on SK (arrow indicates pattern direction). Scale bars, 50 μm. c) results of a modified scratch wound assay show 33% greater coverage of cells within the wounded area after 3d on SK versus SM;

TABLE 1

Sharklet Microtopographies to be tested.

| Surface | Height (μm) | Width (μm) | Spacing (μm) | Aspect Ratio |
|---|---|---|---|---|
| +1SK10×5 | 1 | 10 | 5 | 0.1 |
| +10SK10×5 | 10 | 10 | 5 | 1 |
| +10SK50×50 | 10 | 50 | 50 | 0.2 |
| +100SK50×50 | 100 | 50 | 50 | 2 |

Figure 3:
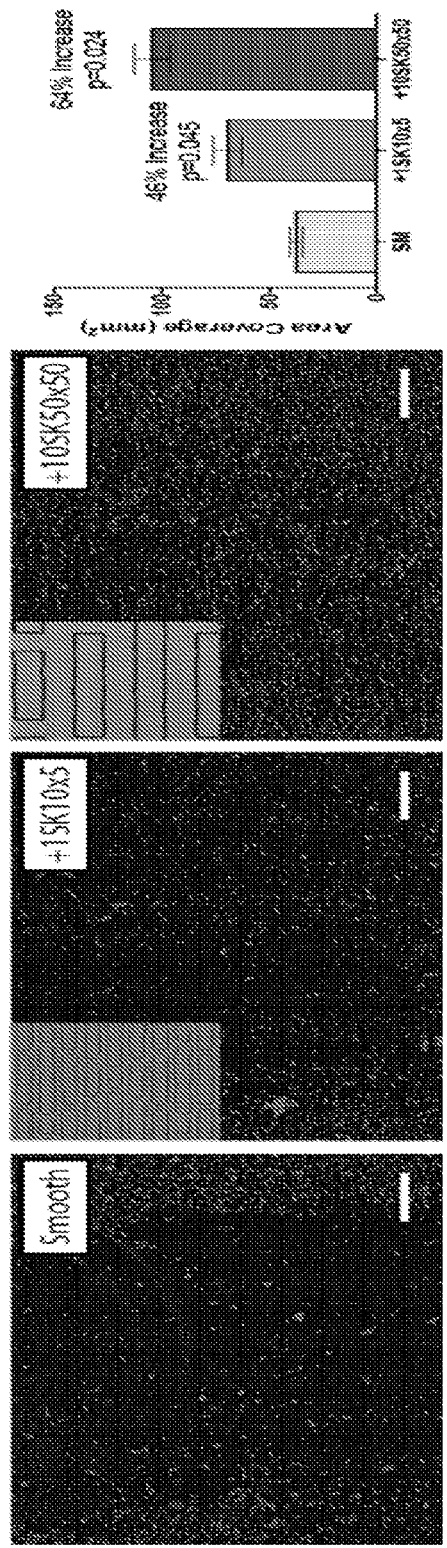
FIG. 3 shows Sharklet™ patterns replicated in biodegradable materials demonstrate increased cell migration and wound closure rates compared to smooth surfaces. Results of a modified scratch wound assay show 46% and 64% greater coverage of cells within the wounded area after 4 days on +1SK10×5 and +10SK50×50, respectively versus smooth.

Preliminary results from testing newly designed Sharklet™ patterns replicated in biodegradable gelatin materials using the same assay as described above show significant increases in cell migration and wound closure rates with increased feature size and aspect ratio (FIG. 3). FIG. 3 shows Sharldet™ patterns replicated in biodegradable materials demonstrate increased cell migration and wound closure rates compared to smooth surfaces. Results of a modified scratch wound assay show 46% and 64% greater coverage of cells within the wounded area after 4 days on +1SK10×5 and +10SK50×50, respectively versus smooth.

Example 2

As our knowledge of the complexities of wound healing has evolved, the wound dressing market has grown accordingly. The requirements for replacing lost skin greatly depend on the type and degree of the wound, as injuries result in loss of skin structure to varying degrees. Superficial wounds result in loss of the outermost layer of the skin, or the epidermis. This layer maintains the barrier function of the skin and consists mainly of epithelial cells called keratinocytes. In more serious injuries, the loss of the epidermal layer and part or all of the dermis (e.g., a partial or full-thickness wound, respectively) results in the need to replace or reconstruct two vital tissue types to restore skin integrity. Dermis is a connective tissue responsible for the mechanical properties of skin. It is composed mainly of fibroblasts and their associated extracellular matrix (ECM). Skin wound healing progresses in four precisely integrated phases: hemostasis, inflammation, proliferation and remodeling. For a wound to heal successfully, all four phases must proceed with proper sequence and timing. A Sharklet micropatterned, full-thickness wound treatment will be the first available dressing that simultaneously accelerates two key steps in the proliferation phase: vascularization and re-epithelialization.

Vascularization, or the formation of new blood vessels in the wound bed, facilitates the formation of granulation tissue, which provides a foundation for re-epithelialization. Re-epithelialization, or the coverage of the wound by new skin cells, is the optimal functional and aesthetic outcome for wound healing.

Figure 4:
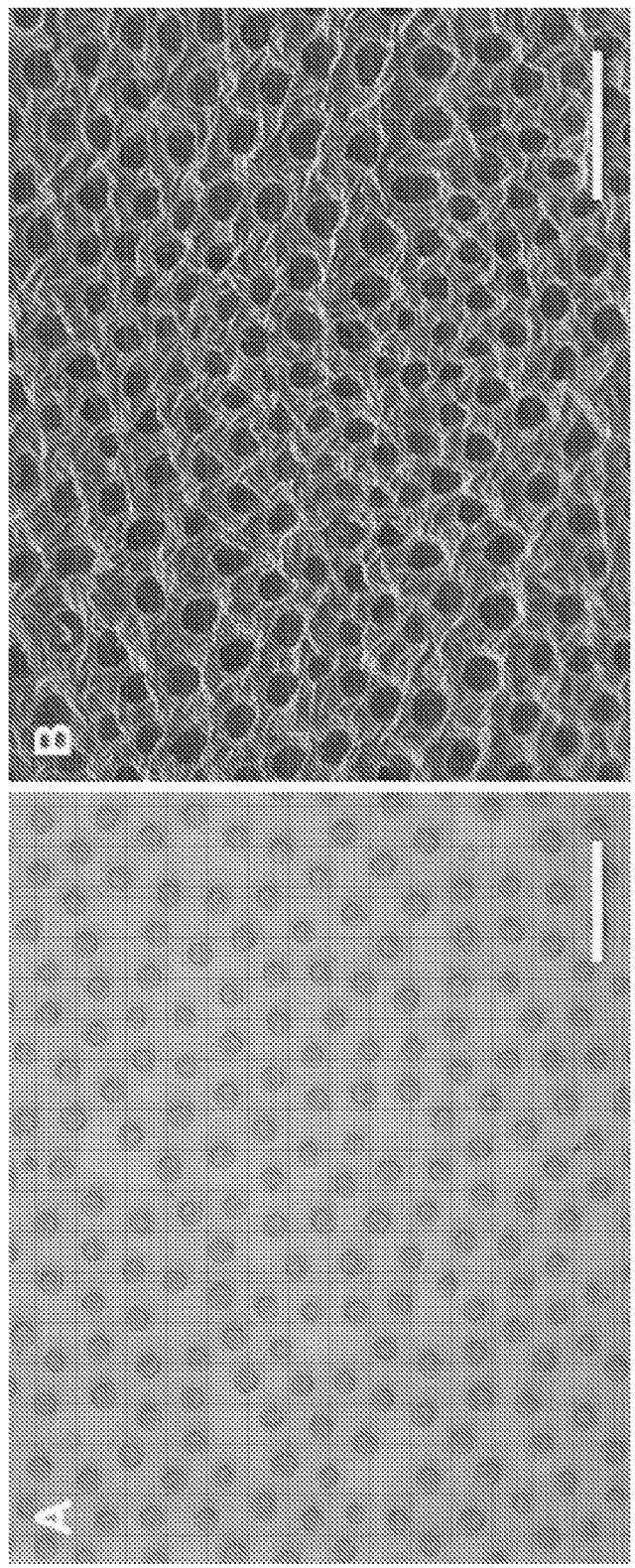
FIG. 4 shows 3-D channel structure in the first layer through which cell growth can occur. This image is specifically for CAPGEL™ materials but other materials may be used to make a similar 3-D structure.

The orientation and polarization (i.e., elongation) of cells in response to the physical properties of the underlying substratum is known as contact guidance. This phenomenon is a key regulator of angiogenesis—new blood vessel formation—and cellular migration. The capacity of physical guidance accelerates vascularization of the wound bed as well as coverage of the wound surface via a bilayered, Sharklet micropatterned wound dressing. The first layer will consist of CAPGEL™, an injectable alginate-based material that forms regularly ordered, tunable anisotropic channels through self-assembly. The 3D microchannel architecture (see FIG. 4) that forms within CAPGEL™ has been shown to support blood vessel infiltration in a rat myocardial infarction model. It has also been shown that dermal revascularization after full-thickness wounding proceeds via ingrowth of vessels from the wound edges through previously formed channels. It is believed that liquid CAPGEL™ injected into even the most complex full-thickness wound bed can form the foundation of a bilayer dressing that will promote neovascularization and granulation tissue formation.

The dermal foundation created by the CAPGEL™ technology will accelerate epidermal healing on the apical Sharklet micro-patterned surface of the wound dressing. Coverage of a wound by keratinocytes or reepithelialization is viewed as a hallmark of successful wound healing. Re-epithelialization by proliferation and migration of keratinocytes starts within 72 hours of injury and continues for approximately 14 days. During the proliferation healing stage, cell migration is a valuable element of the healing process. The Sharklet micropattern uses contact guidance at the apical layer to actively orient the direction and speed of migration to predictably accelerate wound closure. As a result, early re-epithelialization will not only reduce risk of infection and lower patient pain, but it will also initiate the remodeling of underlying granulation tissue, which reduces the possibility of hypertrophic scarring. Without an innovative full-thickness wound-care dressing, both the tissue structure of the dermal basal lamina and the organization of extracellular matrix (ECM) fibers produced by dermal fibroblasts guide fibroblast and epithelial cell migration, respectively, from the wound margins. In fact, the dermal/epidermal junction in native skin is not flat, but consists of a series of micro-scale ridges and projections. These physical cues modulate keratinocyte maturation, differentiation and function, and in turn are essential for tissue organization and integrity of skin structure. These principles can be leveraged synthetically to achieve similar outcomes more efficiently—e.g., simple channels 150 µm deep and 50 µm wide enhanced re-epithelialization rates and resulted in tissue structure similar to that achieved by the same cells cultured on acellular dermis. Likewise, microgrooves 1 µm and 5 µm deep with groove spacing from 1 µm to 10 µm enhance and direct migration of individual epithelial cells and cells from intact epithelial tissue. This shows that micro-topographies direct migration of cells regardless of whether the physical cues present at a wound margin are biotic or abiotic. Therefore, a Sharklet micro-patterned dressing will enhance the wound-healing environment by guiding apical cell proliferation and migration to achieve rapid epidermal wound closure, while also guiding cellular invasion and capillary growth within the underlying dermis.

Example 3

The top-performing Sharklet micropattern (+10SK50×50) from the HEK migration assay was scaled up to the appropriate size for a wound dressing and tested in an established delayed-healing model in rats to validate healing behavior for a broad range of non-healing/chronic wounds. The apical layers of the wound-dressing prototypes were produced following the same procedure outlined above to make gelatin hydrogels. Then the solution-filled molds were cooled to 4° C. for 1 hour to solidify the gelatin. Next, 2 ml of CAPGEL™ slurry was synthesized as previously described and packed into a PDMSe mold (d=20 mm) on top of the solid gelatin. The apical gelatin layer and the basement CAPGEL™ layers were chemically crosslinked with a solution of 0.6M EDC and 0.2M NHS in PBS at 4° C. for 18 hours. The silicone mold was removed from the construct and a 6-mm biopsy punch was used to create appropriately sized dressings. The dressings were then washed in PBS for 1 hour and followed by three changes of 10× Saline Sodium Citrate (SSC) (20×SSC, Fisher BioReagants, diluted with deionized water to 10×) over the course of 24 hour. Finally, dressings were washed with three changes of normal saline over the course of 24 hour and subsequently sterilized by soaking in Minncare Sterilant (3% solution in deionized water) (Mar Cor, Plymouth Minn.) for ten minutes prior to a final PBS rinse and implantation.

All animal experiments were conducted under a protocol approved by the University of Florida Animal Care and Use Committee and in compliance with the standards in the "Guide for Care and Use of Laboratory Animals" published by the National Institutes of Health (NIH). After appropriate anesthetization, the dorsal aspect of 20 male Sprague-Dawley rats weighing ~250-300 g were shaved and a rectangular template was centered on the spine between the base of the scapula and the iliac crest. The template was used to outline the placement of four circular holes and the placement of vertical tissue-flap incisions. Four full-thickness wounds were created at the corresponding markings using a 6-mm biopsy punch. These normal skin punches were fixed in 10% neutral buffered formalin for subsequent analysis. To create a condition of transient ischemia, two parallel linear incisions were cut along the sides of the template. The skin flap created was elevated to sever the underlying vasculature, repositioned, and stapled on each lateral side. One of each of the four dressings: 1) the novel bilayer Sharklet micropatterned apical layer with the combined CAPGEL™ neovascularization technology, 2) a smooth apical layer with CAPGEL™, 3) Endoform, a dermal template that is currently in clinical use as a commercial competitor and 4) no treatment. The endoform dermal template consists of a naturally derived ovine collagen ECM. All wounds were covered with a compressible secondary dressing and covered with Vetrap (3M).

On post-surgery days 7, 10 and 14, rats (N=6) were euthanized. Two rats were also euthanized on post-surgery day 28 to qualitatively observe the extent of dressing degradation. Tissue biopsies were collected using 8-mm biopsy punches, fixed in 10% neutral buffered formalin, embedded in paraffin, sectioned and stained with either hematoxylin and eosin (H&E) or Masson's Trichrome. Histological wound sections were evaluated by a veterinary pathologist, board certified by the American College of Veterinary Pathologists, for dressing location, re-epithelialization, acute and chronic inflammation, granulation tissue formation and neovascularization using an established, semi-quantitative histologic scoring scale (Table 2). Results were analyzed to assess clinically relevant outcomes of each treatment that enhance the wound-healing environment—e.g., epithelial coverage, vascularization and overall wound healing, a composite score including all measured outcomes.

Ischemic Wound Model

Qualitative assessment of representative photomicrographs of H&E stained sections of rat skin 7 days post-wounding (FIG. 5b) show indications of improved healing outcomes for wounds treated with bilayered dressings compared to untreated controls. Untreated wounds, in general, exhibited higher levels of contraction, incomplete re-epithelialization and differences in dermal structure compared to unwounded skin (FIG. 5c). Both bilayered dressing constructs showed more complete re-epithelialization, reduced contracture compared to untreated or Endoform-treated wounds and dermal regeneration that more closely mimics natural skin (FIGS. 5d and 5e). Wounds treated with Endoform, a clinically available dermal template dressing, exhibit higher levels of contraction than those dressed with the bilayered constructs, incomplete epithelialization and reduced amount and maturity of granulation tissue formation on Day 7 (FIG. 5f).

Semi-quantitative wound-healing scores from histologic grading reveal that bilayered constructs improve overall healing compared to untreated wounds and these improvements are not statistically different from those measured on Endoform-treated wounds (FIG. 6a). Composite wound-healing scores include evaluation of dressing location, re-epithelialization, acute and chronic inflammation, granulation tissue formation and neovascularization. All dressings, smooth, Sharklet-patterned and Endoform exhibited increases in composite mean wound healing scores compared to no treatment at 7 (22% increase, p≤0.05), 10 (32% increase, p≤0.001) and 14 (31% increase, p≤0.05) days post-wounding. Evaluation of re-epithelialization showed no significant differences among groups (FIG. 6b). The average wound-healing scores for neovascularization demonstrated increases for all treatment groups over the no treatment negative controls but no significant differences among treatment groups. The dressings resulted in more blood vessels per field of high powered view (40× magnification) over untreated controls at 10 (14%, p≤0.05) and 14 (29%, p≤0.001) days post-wounding (FIG. 6c). Qualitative observations (N=2) of H&E stained sections of rat skin 28 days post-wounding demonstrated that the bilayered, hydrogel dressings degraded in vivo over this period of time (FIG. 7).

TABLE 2

Quantitative wound-healing histologic scoring system.

| Variable | Score 0 | Score 1 | Score 2 | Score 3 |
| --- | --- | --- | --- | --- |
| Dressing | None noted | Majority/all noted under epidermis or within dermis | Majority/all noted superficially or above dermis | N/A |
| Re-epithelialization | None; significant epidermal defect | Partial, incomplete, discontinuous | Complete with epidermis of normal thickness | Complete but hyperplastic epidermis |
| Acute Inflammation (presence of neutrophils) | None | Scant | Moderate | Abundant |
| Chronic Inflammation (presence of lymphocytes, plasma cells, macrophages) | None | Scant | Moderate | Abundant |
| Granulation Tissue | None | Scant; partial across wound gap or depth; immature, loose | Moderate; partial across wound gap or depth; immature, loose | Abundant; complete across wound gap and entire depth; mature, dense |
| Neovascularization | None | Up to 5 vessels per high-powered field of view (40x magnification) | 6 to 10 vessels per high-powered field of view (40x magnification) | Greater than 10 vessels per high-powered field of view (40x magnification) |

Figure 5:
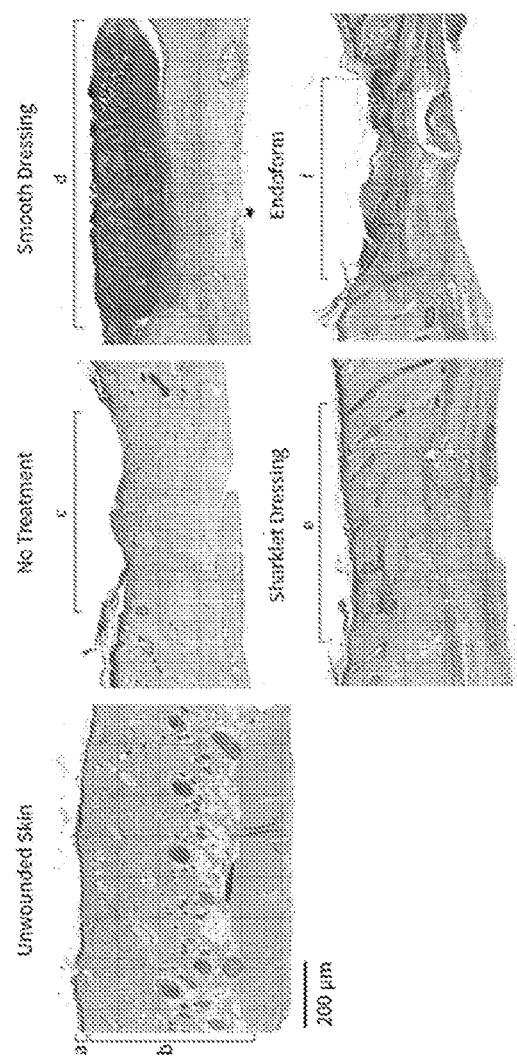
FIG. 5 shows representative photomicrographs of H&E stained sections of rat skin 7 days post-wounding.

FIG. 5 shows representative photomicrographs of H&E stained sections of rat skin 7 days post-wounding. a) The structure of the epidermis in unwounded, control rat skin. b) The structure of the dermis in unwounded, control rat skin. c) Indicates the wounded area on the No Treatment group. These wounds exhibit higher levels of contraction, incomplete epithelial coverage and differences in dermal structure compared to native skin. d) Denotes the wounded area on skin treated with the Smooth dressing. In this image the dressing is not completely incorporated below the epidermis (Score 2), epithelialization is incomplete and the structure of the dermis is not consistent with unwounded skin. e) Shows the wounded area on skin treated with the Sharklet dressing. These wounds exhibit complete re-epithelialization, reduced contracture compared to no treatment or Endoform-treated wounds and a dermal structure that more closely mimics natural skin. f) Indicates the wounded area treated with Endoform, a clinically available dermal template dressing. Wounds treated with Endoform demonstrate higher levels of contraction than those dressed with the bilayered constructs, incomplete epithelialization and reduced amounts and maturation of granulation tissue formation on Day 7.

Figure 6:
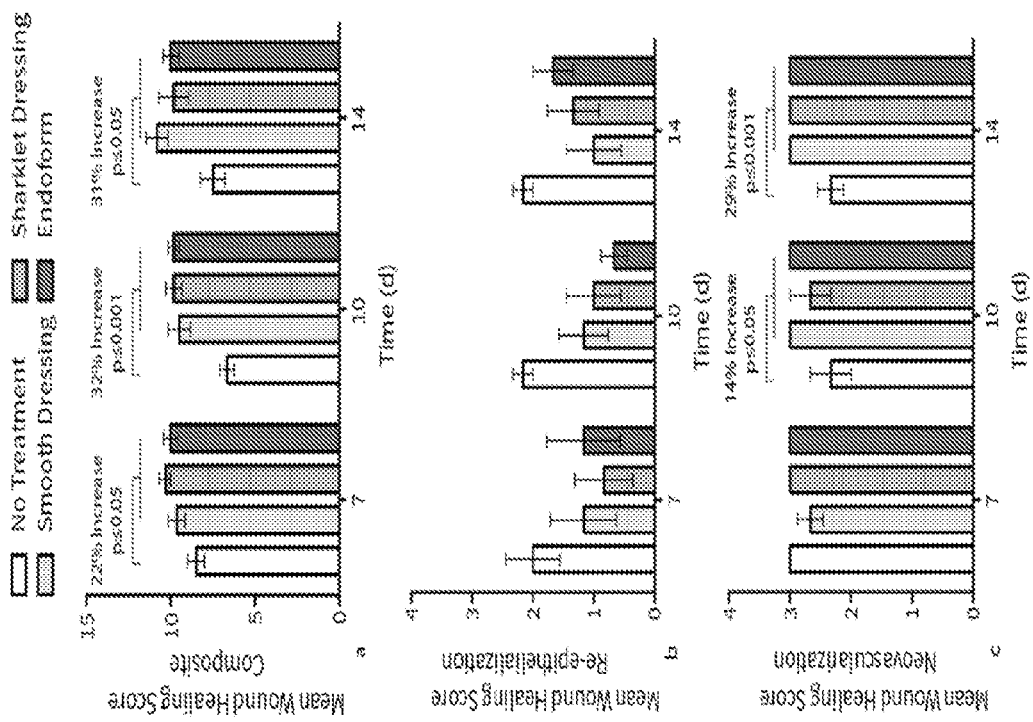
FIG. 6 is a graph that shows histologic wound-healing scores.
Figure 7:
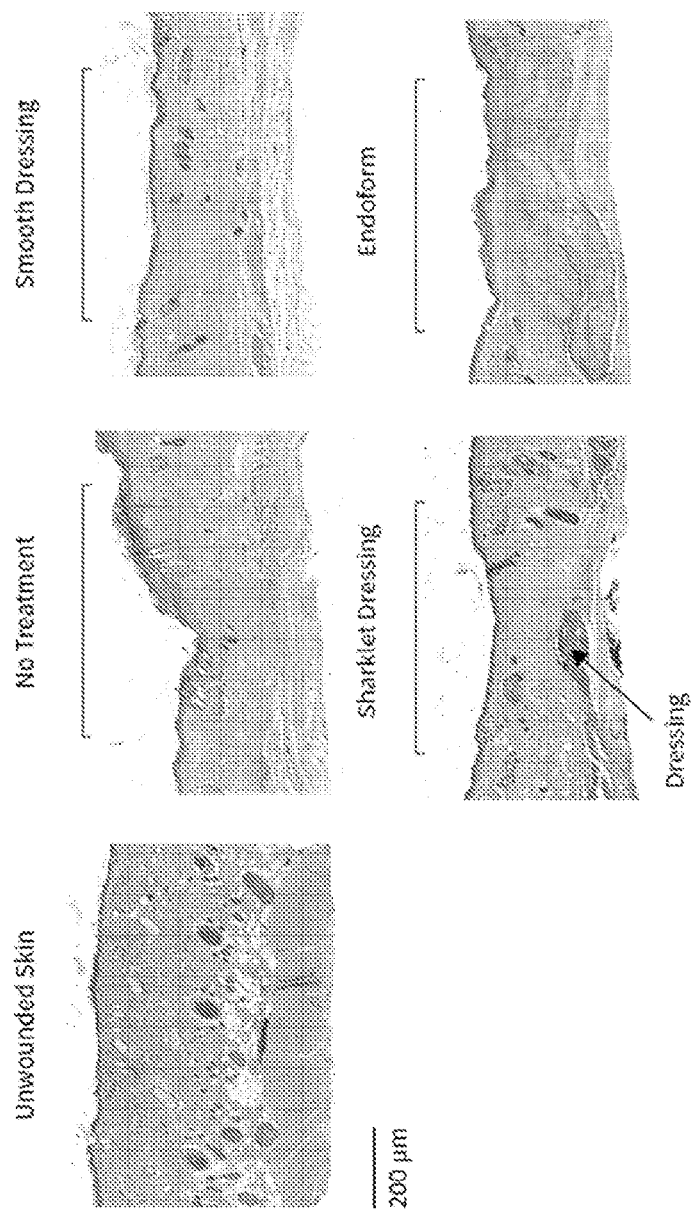
FIG. 7 includes representative photomicrographs of H&E stained sections of rat skin 28 days post-wounding. This figure demonstrates degradation of the wound dressing over time in vivo.

FIG. 6 shows histologic wound-healing scores. a) Mean overall wound healing score composite including grading for dressing location, re-epithelialization, acute and chronic inflammation, granulation tissue formation and neovascularization. All dressing types showed significantly improved healing versus no treatment. Statistically significant increases over no treatment are reported for all dressings, which were not significantly different among groups. b) Mean re-epithelialization scores indicate no significant differences among treatment groups. c) Mean neovascularization results show higher numbers of new blood vessels formed in wounds treated with dressings versus no treatment but no significant differences among dressing types. Overall improved healing versus no treatment and outcomes comparable to a standard care treatment, i.e., the Endoform dermal template, demonstrate potential for the bilayered wound dressing constructs to improve healing outcomes.

FIG. 7 includes representative photomicrographs of H&E stained sections of rat skin 28 days post-wounding. These images show qualitatively that the bilayered, hydrogel dressings degraded completely over 28 days in vivo. The arrow indicates only a small piece of dressing remained in the tissue of the wound implanted with a Sharklet-patterned dressing. There is no dressing visible in the wound treated with a smooth, bilayered dressing.

It is to be understood that while the invention has been described in conjunction with the preferred specific embodiments thereof, that the foregoing description as well as the examples, which follow are intended to illustrate and not limit the scope of the invention. Other aspects, advantages and modifications within the scope of the invention will be apparent to those skilled in the art to which the invention pertains.

What is claimed is:

1. A multilayered wound dressing comprising: a first layer; the first layer comprising channels that facilitate neovascularization of a wound; wherein the first layer comprises a gel; and a second layer in direct contact with the first layer, the second layer having the same or different chemical composition as the first layer; wherein the second layer comprises at least one surface that has a texture that comprises a plurality of spaced features; wherein each feature has a substantially different geometry than a neighboring feature; the plurality of spaced features arranged in a plurality of groupings, the spaced features within each of the groupings being spaced apart at an average distance of about 10 nanometers to about 200 micrometers; the adjacent groupings of features being spaced from each other to define an intermediate tortuous pathway; wherein a direction of the texture is operative to facilitate cell orientation and growth and wherein the textured surface of the second layer does not contact the first layer.

2. The multilayer wound dressing of claim 1, wherein the first layer comprises a surface that has a texture that is complementary to a patient's anatomy where the wound is located.

3. The multilayer wound dressing of claim 1, wherein the first layer and the second layer are biodegradable layers.

4. The multilayer wound dressing of claim 1, wherein the gel comprises a copper capillary alginate gel.

5. The multilayer wound dressing of claim 4, wherein the copper capillary alginate gel is stabilized with barium ions.

6. The multilayer wound dressing of claim 4, wherein the copper capillary alginate gel is stabilized using $Cd^{2+}$, $Cu^{2+}$, $Ca^{2+}$, $Ni^{2+}$, $Co^{2+}$, and $Mn^{2+}$.

7. The multilayer wound dressing of claim 1, wherein the first layer and the second layer comprise polylactic-glycolic acid (PLGA), poly-caprolactone (PCL), copolymers of poly-lactic-glycolic acid and poly-caprolactone (PCL-PLGA copolymer), polyhydroxy-butyrate-valerate (PHBV), poly-orthoester (POE), polyethylene oxide-butylene terephthalate (PEO-PBTP), poly-D,L-lactic acid-p-dioxanone-polyethylene glycol block copolymer (PLA-DX-PEG) or a combination comprising at least one of the foregoing polymers.

8. The multilayer wound dressing of claim 1, wherein the first layer and the second layer comprise a copolymer of polyurethane and poly lactic acid or a copolymer of polyurethane and polylactic-glycolic acid.

* * * * *